United States Patent
Park et al.

(10) Patent No.: US 10,631,897 B2
(45) Date of Patent: Apr. 28, 2020

(54) EXTERNAL FIXATOR AND EXTERNAL FIXING SYSTEM

(71) Applicant: KYUNGPOOK NATIONAL UNIVERSITY INDUSTRY-ACADEMIC COOPERATION FOUNDATION, Daegu (KR)

(72) Inventors: Ilhyung Park, Daegu (KR); Changwuk Oh, Daegu (KR); Hyunwoo Lee, Daegu (KR); Sanghyun Joung, Daegu (KR); Chulwoo Park, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 0 days.

(21) Appl. No.: 16/072,847

(22) PCT Filed: Sep. 1, 2016

(86) PCT No.: PCT/KR2016/009763
§ 371 (c)(1),
(2) Date: Jul. 25, 2018

(87) PCT Pub. No.: WO2017/131309
PCT Pub. Date: Aug. 3, 2017

(65) Prior Publication Data
US 2019/0029727 A1    Jan. 31, 2019

(30) Foreign Application Priority Data
Jan. 26, 2016 (KR) .......................... 10-2016-0009351

(51) Int. Cl.
*A61B 17/66* (2006.01)
*A61B 17/62* (2006.01)
(Continued)

(52) U.S. Cl.
CPC .............. *A61B 17/66* (2013.01); *A61B 17/62* (2013.01); *A61B 17/6416* (2013.01); *A61B 17/645* (2013.01); *A61B 2090/031* (2016.02)

(58) Field of Classification Search
CPC ....... A61B 17/62; A61B 17/64; A61B 17/645; A61B 17/6458; A61B 17/66
See application file for complete search history.

(56) References Cited

U.S. PATENT DOCUMENTS 5,688,271 A     11/1997  Faccioli et al.
2005/0215997 A1  9/2005  Austin et al.
(Continued)

FOREIGN PATENT DOCUMENTS

JP    3157067 U      1/2010
JP    2014-179092 A  9/2014
(Continued)

OTHER PUBLICATIONS

Dror Paley, "History and Science Behind the Six-Axis Correction External Fixation Devices in Orthopaedic Surgery". Operative Techniques in Orthopaedics, Jun. 2011.

*Primary Examiner* — Julianna N Harvey
(74) *Attorney, Agent, or Firm* — Novick, Kim & Lee, PLLC; Sang Ho Lee

(57) ABSTRACT

Provided is an external fixator for reduction of a fractured or deformed bone, which includes a first frame through which the bone passes, a second frame through which the bone passes, the second frame being spaced apart from the first frame, and a variable leg connected to the second frame by a ball joint and having a first leg and a second leg at which a thread is formed respectively. The ball joint includes a ball connected to the first leg through a ball axle and having a perforation hole passing through a center thereof, a ball housing located at the second frame and having a fitting groove into which the ball is fit and a pair of insert holes (Continued)

formed at an outer surface thereof along a direction traversing the fitting groove to face each other, and a pin member provided on the insert hole to pass through the perforation hole. As the ball housing rotates, the first leg rotates to fasten or release screw coupling between the first leg and the second leg and thus change a length of the variable leg.

16 Claims, 8 Drawing Sheets

(51) Int. Cl.
*A61B 17/64* (2006.01)
*A61B 90/00* (2016.01)

(56) References Cited

U.S. PATENT DOCUMENTS

| | | | |
|---|---|---|---|
| 2011/0004199 A1* | 1/2011 | Ross | A61B 17/8875 |
| | | | 606/1 |
| 2014/0276820 A1 | 9/2014 | Cresina et al. | |
| 2015/0265313 A1 | 9/2015 | Wong | |
| 2015/0272624 A1* | 10/2015 | Singh | A61B 17/62 |
| | | | 606/56 |

FOREIGN PATENT DOCUMENTS

| | | |
|---|---|---|
| KR | 20-1999-0023384 U | 7/1999 |
| KR | 10-0399004 B1 | 9/2003 |
| KR | 10-2004-0037221 A | 5/2004 |
| KR | 10-2015-0124469 A | 11/2015 |
| KR | 10-1576798 B1 | 12/2015 |

* cited by examiner

[FIG. 1]
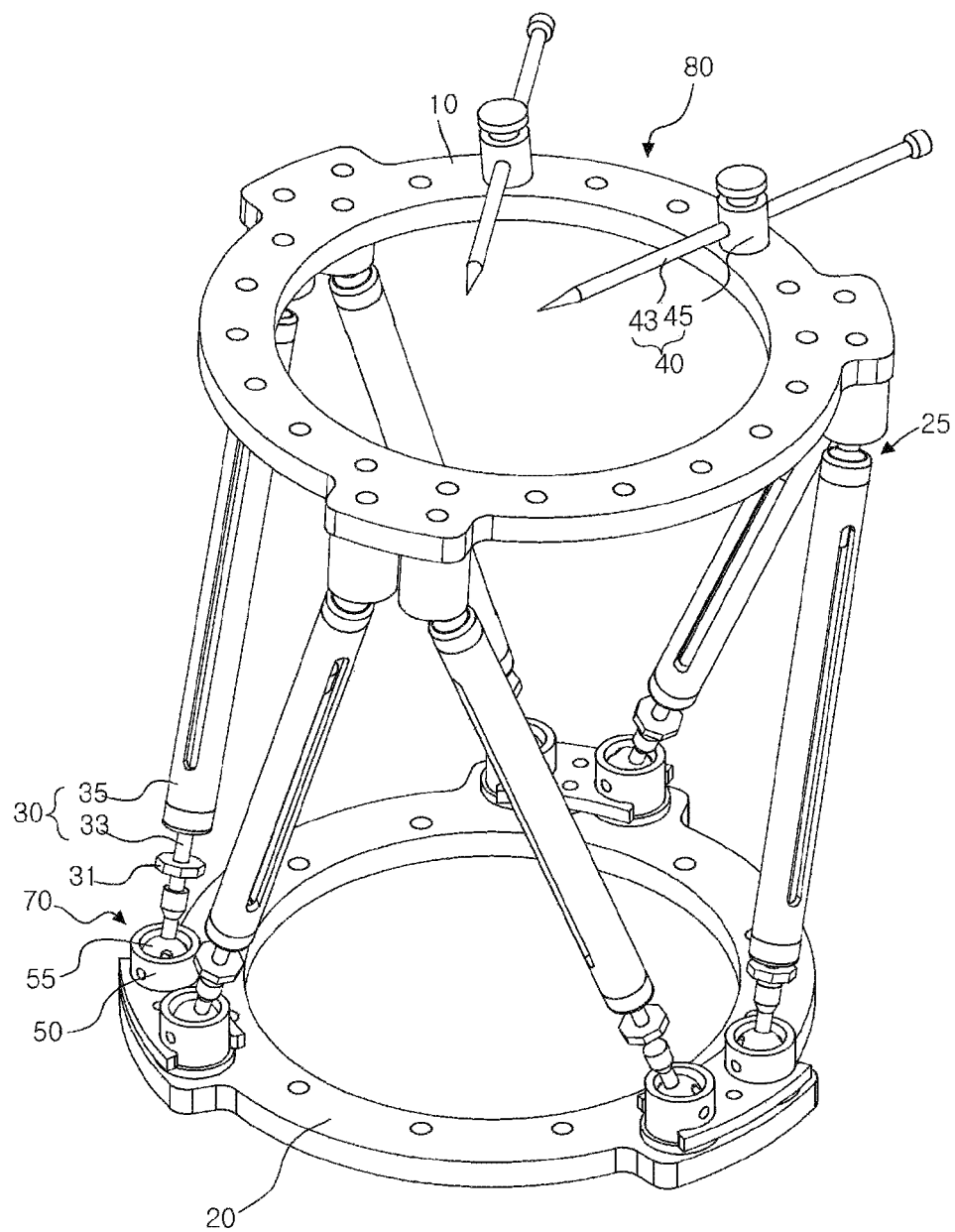

【FIG. 2】
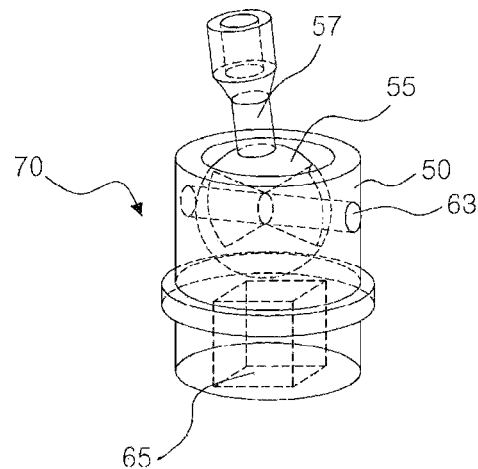
【FIG. 3】
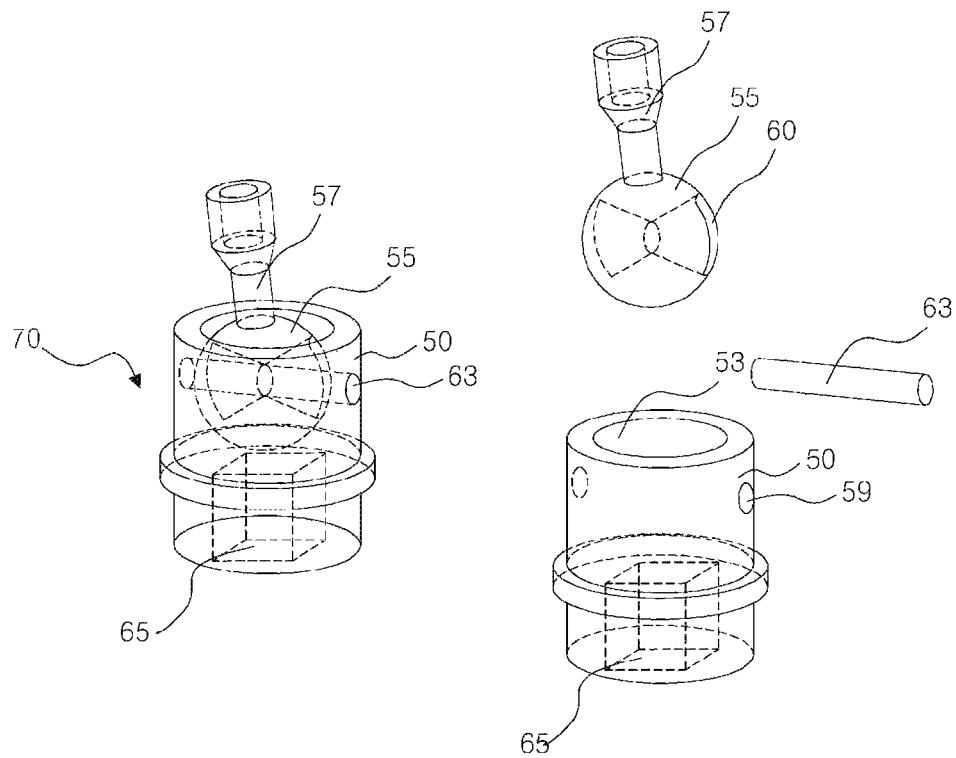

【FIG. 4】
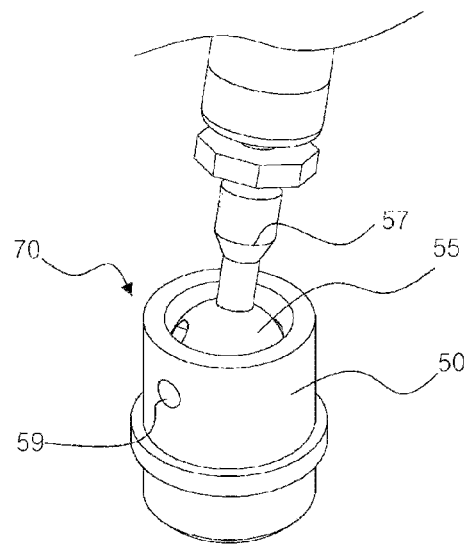
【FIG. 5】
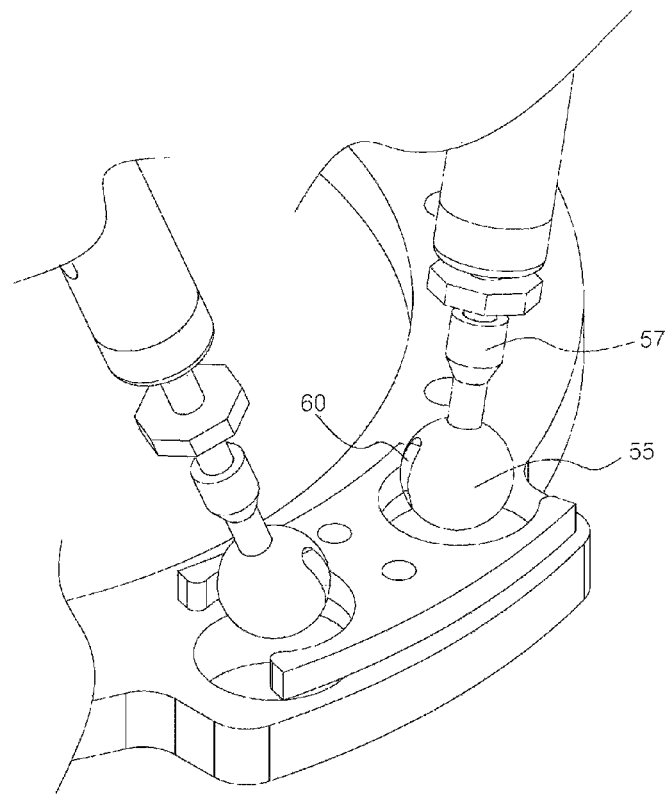

[FIG. 6]
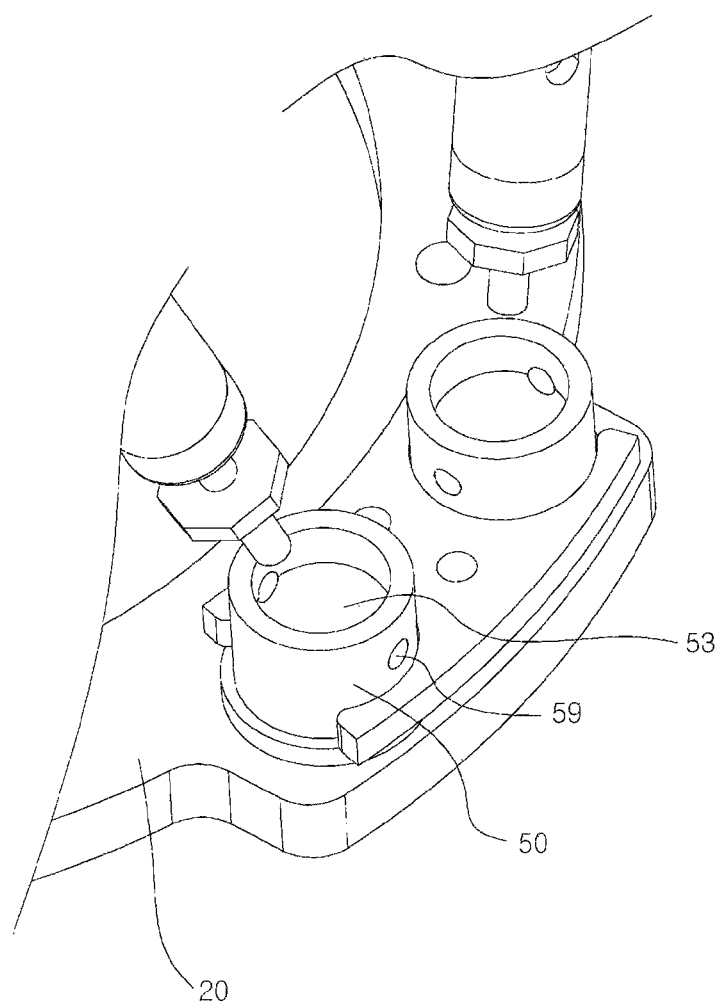

[FIG. 7]
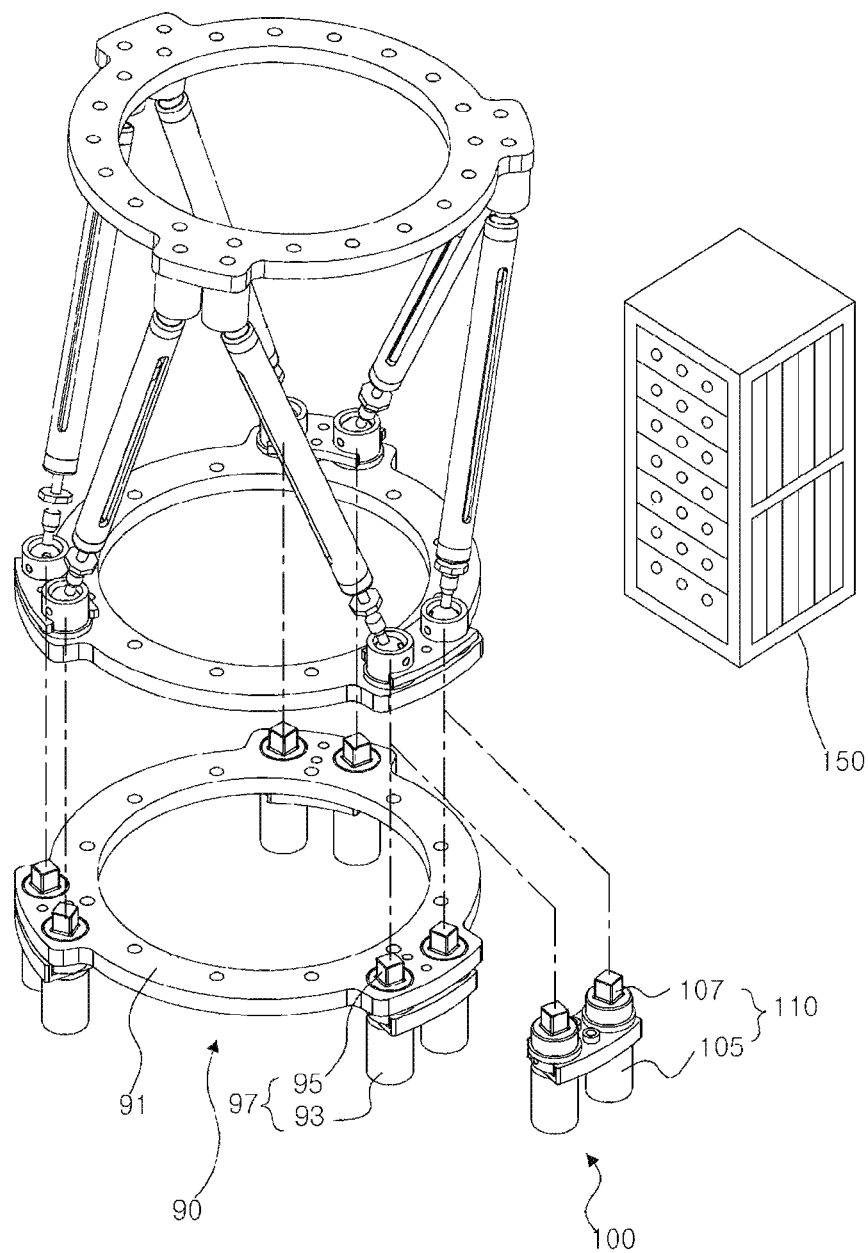

[FIG. 8]
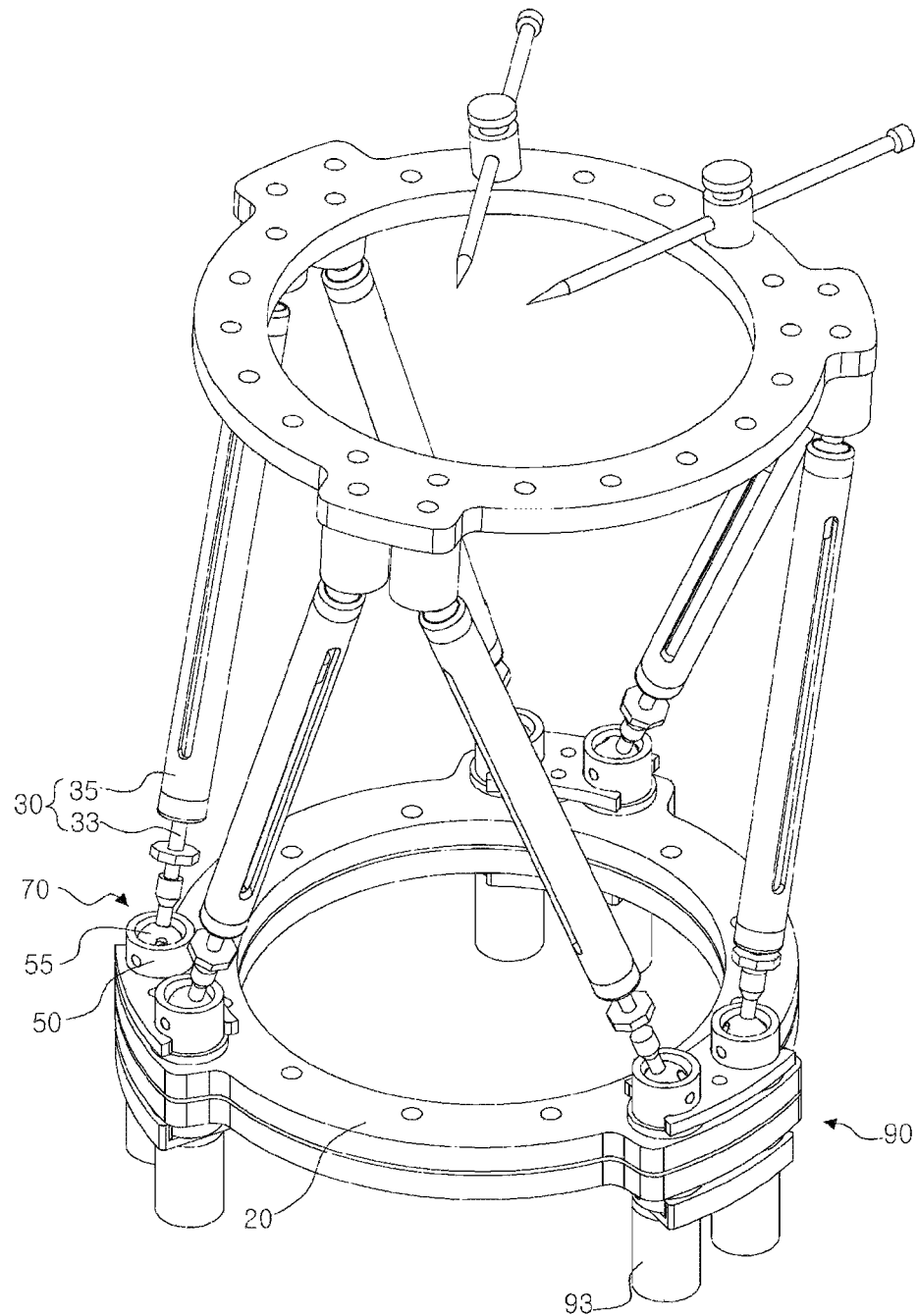

[FIG. 9]
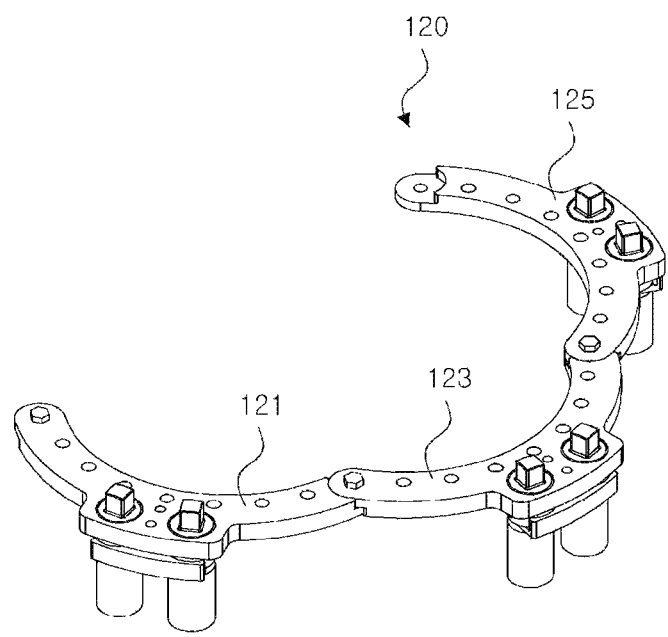

【FIG. 10】
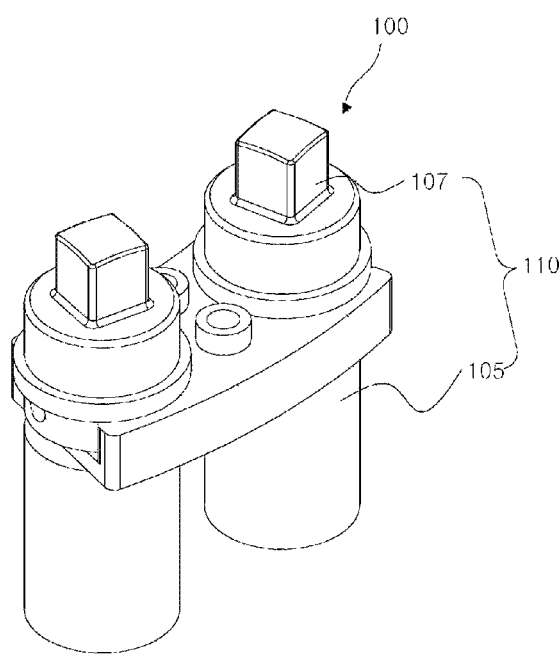
【FIG. 11】
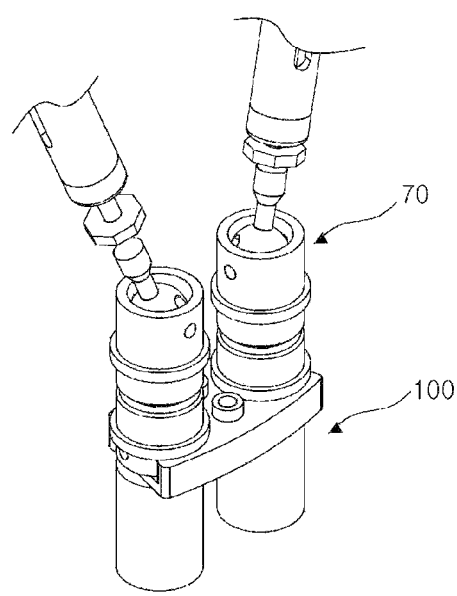

//EXTERNAL FIXATOR AND EXTERNAL FIXING SYSTEM

TECHNICAL FIELD

The present disclosure relates to an external fixator and an external fixing system, and more particularly, to an external fixator and an external fixing system operated by a detachable actuator.

BACKGROUND ART

Minimally invasive fracture reposition surgery is a fracture reposition surgery that minimizes the incision of a patient. In the fracture reposition surgery, a real-time X-ray equipment such as a C-ARM is used for reduction of a displaced bone, and then an intramedullary nail is inserted in the repositioned state to fix the corrected bone fragments.

An external fixator used in the fracture reposition surgery includes a fixing member for fixing a bone fragment of the fractured or deformed bone on an upper frame and a variable leg for connecting the upper frame and the lower frame and changing the lengths of the upper frame and the lower frame to apply a force for reduction to the bone while changing the relative positions of the upper frame and the lower frame.

A conventional external fixator (Korean Patent No. 10-1576798) discloses that an actuator is installed inside a variable leg to change the length of the variable leg, so that it is difficult to use the external fixator since the variable leg has a great weight and volume due to the actuator. In addition, since the actuator made of metal is located in the variable leg, a radiograph should be taken several times because if the radiograph is not taken smoothly and accordingly, a medical worker and the patient is more exposed to the radiation.

DISCLOSURE

Technical Problem

In order to solve the above problems, it is necessary to consider a method of operating an actuator for changing the length of a variable leg in a detachable manner, instead of installing the actuator inside the variable leg. Also, it is necessary to design a connection structure between the detachable actuator and an external fixator such that the detachable actuator is useable for the external fixator.

The present disclosure is directed to provide an external fixator and an external fixing system that are easy to use and carry by utilizing a detachable actuator for the external fixator and are capable of reducing the radiation dose of medical workers and patients.

The objects to be solved by the present disclosure are not limited to the above, and other objects not mentioned herein can be clearly understood from the following disclosure by those skilled in the art.

Technical Solution

In one aspect, there is provided an external fixator for reduction of a fractured or deformed bone, comprising: a first frame through which the bone passes; a second frame through which the bone passes, the second frame being spaced apart from the first frame; and a variable leg connected to the second frame by a ball joint and having a first leg and a second leg at which a thread is formed respectively, wherein the ball joint includes a ball connected to the first leg through a ball axle and having a perforation hole passing through a center thereof, a ball housing located at the second frame and having a fitting groove into which the ball is fit and a pair of insert holes formed at an outer surface thereof along a direction traversing the fitting groove to face each other, and a pin member provided to extend over the insert holes to pass through the perforation hole, and wherein as the ball housing rotates, the first leg rotates to fasten or release screw coupling between the first leg and the second leg and thus changing a length of the variable leg.

In another aspect of the present disclosure, there is also provided an external fixing system including an external fixator defined in the embodiment, the external fixing system comprising: a detachable actuator configured to give a power to rotate the ball housing and having a motor and a power transmission member rotated by the motor; and a planning server configured to select a motor to be operated and control a rotating force and a rotating direction of the operated motor, wherein a protrusion of the power transmission member is inserted into a lower space of the ball housing so that the ball housing rotates by a rotation force of the actuator.

Advantageous Effects

According to the present disclosure, it is possible to provide an external fixator and an external fixing system that are easy to use and carry by utilizing a detachable actuator for the external fixator and are capable of reducing the radiation dose of medical workers and patients.

DESCRIPTION OF DRAWINGS

FIG. 1 is a perspective view showing an external fixator according to an embodiment of the present disclosure.

FIG. 2 is a projective view showing a ball joint of the external fixator according to an embodiment of the present disclosure.

FIG. 3 is an exploded view showing the ball joint of the external fixator according to an embodiment of the present disclosure.

FIGS. 4 to 6 are diagrams showing partial configurations of the ball joint of the external fixator according to an embodiment of the present disclosure.

FIG. 7 is a diagram showing an external fixing system according to an embodiment of the present disclosure.

FIG. 8 is a diagram showing that a surgical actuator is coupled to an external fixator of the external fixing system according to an embodiment of the present disclosure.

FIG. 9 is a diagram showing another example of the surgical actuator of the external fixing system according to an embodiment of the present disclosure.

FIG. 10 is a perspective view showing a portable actuator of the external fixing system according to an embodiment of the present disclosure.

FIG. 11 is a schematic view showing that a portable actuator and a ball housing of the external fixing system according to an embodiment of the present disclosure are coupled.

REFERENCE SIGNS

| 10: first frame | 20: second frame |
|---|---|
| 25: spherical joint | 30: variable leg |

-continued

| | |
|---|---|
| 31: shaft fixing device | 33: first leg |
| 35: second leg | 40: fixing member |
| 43: pin | 45: fixture |
| 50: ball housing | 53: fitting groove |
| 55: ball | 57: ball axle |
| 59: insert hole | 60: perforation hole |
| 63: pin member | 65: lower space |
| 70: ball joint | 80: external fixator |
| 90: surgical actuator | 91, 120: motor frame |
| 93, 105: motor | 95, 107: motor drive |
| 97, 110: driving unit | 100: portable actuator |
| 121, 123, 125: sub frame | 150: planning server |

BEST MODE

The advantages and features of the present disclosure and the method for accomplishing the same will be apparent from the following description with reference to the accompanying drawings. However, the present disclosure is not limited to the embodiments described herein but can be implemented in various ways. The embodiments are just to make the present disclosure to be completely understood by those skilled in the art, and the present disclosure is defined only by the scope of the claims. Throughout the drawings, like reference signs refer to like components.

The terminology used herein is for the purpose of describing particular embodiments only and is not intended to limit the present disclosure. In the specification, the singular forms are intended to include the plural forms as well, unless the context clearly indicates otherwise. It will be further understood that the terms "comprises" and/or "comprising" used in this specification do not preclude the presence or addition of one or more other elements, steps and operations.

An external fixator according to an embodiment of the present disclosure will be described with reference to FIGS. 1 to 6. FIG. 1 is a perspective view showing an external fixator according to an embodiment of the present disclosure. FIG. 2 is a projective view showing a ball joint of the external fixator according to an embodiment of the present disclosure. FIG. 3 is an exploded view showing the ball joint of the external fixator according to an embodiment of the present disclosure. FIGS. 4 to 6 are diagrams showing partial configurations of the ball joint of the external fixator according to an embodiment of the present disclosure.

Referring to FIGS. 1 to 6, an external fixator 80 according to an embodiment of the present disclosure is an external fixator for reduction of the fractured or deformed bone and includes a first frame 10, a second frame 20, a variable leg 30, a ball joint 70 and a fixing member 40.

The first frame 10 and the second frame 20 constitute both end portions and upper and lower portions of the external fixator 80. In some cases, the first frame 10 may be regarded as an upper frame and the second frame 20 may be regarded as a lower frame. The first frame 10 and the second frame 20 have a perforation therein so that the bone of the arm or leg of a patient may pass through the inside of the first frame 10 and the second frame 20. Since the first frame 10 and the second frame 20 have a perforation as above, the external fixator 80 may surround a fractured or deformed part of the bone. The perforation may have various shapes, such as circular and polygonal shapes, and there is no limit to the shape as long as it is possible to surround the arm or leg of the patient.

Meanwhile, at least one of the first frame 10 and the second frame 20 may be composed of a plurality of sub frames, and the sub frames may be connected using a coupling component as a bolt and a nut. If the first frame 10 or the second frame 20 is composed of a plurality of sub frames, it is not needed to mount an external fixing device from an end of the leg or arm of a patient so that the external fixator 80 surrounds the fractured or deformed part of the bone. Instead, after releasing the coupling between the sub frames and opening the released sub frames, the external fixator 80 may be immediately attached to the fractured or deformed part of the bone.

The variable leg 30 is a member connecting the first frame 10 and the second frame 20 since one end thereof is connected to the first frame 10 and the other end thereof is connected to the second frame 20. In addition, the variable leg 30 includes a first leg 33 having a male thread and a second leg 35 having a female thread to make screw coupling with the male thread. The entire length of the variable leg 30 may vary by fastening or releasing the screw coupling between the male thread and the female thread, and as a result, the relative positions and postures of the first frame 10 and the second frame 20 may be changed.

Also, the variable leg 30 may be connected to the first frame 10 through a spherical joint 25 and may be connected to the second frame 20 through a ball joint 70. Here, the angle formed by the first frame 10, the second frame 20 and the variable leg 30 may vary. Due to the change in the length of the variable leg 30 and the characteristics of the spherical joint 25 and the ball joint 70, the external fixator 80 may effectively perform external fixation with respect to the bone fractured or deformed in various forms.

In addition, a nut-like shaft fixing device 31 may be provided to the first leg 33 having a male thread. The shaft fixation device 31 may have a nut shape and thus may make screw coupling with the male thread of the first leg 33 to be located at the first leg 33 and may also be moved up and down on the first leg 33 by fastening or releasing the screw coupling. Seeing the shaft fixing process of the shaft fixation device 31, when it is necessary to fix the length of variable leg 30 not to be changed after the external fixation surgery for the reduction of a fractured or deformed bone is completed (namely, after an actuator for changing the length of external fixation 30 is removed), the shaft fixing device 31 is moved on the first leg 33 to a position where the shaft fixing device 31 comes into contact with a lower end of the second leg 35 so that the second leg 35 is prevented from moving downward. By doing so, the length of the shaft that is the variable leg 30 may be fixed without changing. Since the shaft fixing device 31 prevents the length of the variable leg 30 from changing in this way, the bone may maintain its reduced shape even after the surgical operation, thereby ensuring excellent bone reduction effect.

Meanwhile, the number of variable legs 30 may be six, but the number of variable legs 30 may vary depending on the type and purpose of surgical operation.

The ball joint 70 is a member for connecting the variable leg 30 and the second frame 20 serving as a lower frame and may include a ball axle 57 connected to the first leg 33 of the variable leg 30, a ball 55 formed at an end of the ball axle 57, a ball housing 50 installed at the second frame 20 and having a fitting groove 53 into which the ball 55 is fit, and a pin member 63.

In addition, the ball 55 has a perforation hole 60 passing through the center of the ball 55. Also, a pair of insert holes 59 is formed at an outer surface of the ball housing 50 to face each other along a direction traversing the fitting groove 53. As the pin member 63 having a rod shape passes through one insert hole 59 of the ball housing 50, passes through the perforation hole 60 of the ball 55, and then passes through the other insert hole 59 of the ball housing 50, the pin member 63 may extend over the pair of insert holes 59 and simultaneously pass through the perforation hole 60 of the ball 55.

Moreover, the perforation hole 60 of the ball 55 may have the same diameter as the pin member 63 at the center thereof, and thus the pin member 63 may engage with the perforation hole 60 at the center of the ball 55. Meanwhile, as seen from FIG. 6, a portion of the perforation hole 60 on a spherical surface of the ball 55 may have a slit shape, and the area of the slit shape is larger than a sectional area of the pin member 63, thereby ensuring the pivot movement of the ball 55.

In addition, a lower space 65 is formed in the lower part of the ball housing 50, and a protrusion of the actuator, explained later, is inserted into the lower space 65. Thus, the rotation force of the actuator is transmitted to the ball housing 50 to rotate the ball housing 50.

The ball housing 50 is installed on the second frame 20. For the installation, in the present disclosure, two ball housings 50 adjacent to each other form one group, and three groups in total are installed at a predetermined interval on the second frame 20. However, the installation method of the ball housing 50 may be performed in various ways and is not limited to the above.

In relation to the structure of the ball housing 50 and the length change of the variable leg 30, a means for changing the length of the variable leg 30 is not provided inside the variable leg 30. Instead, due to the structure of the ball housing 50 as described above, an actuator provided separately from the external fixator 80 is used to rotate the ball housing 50, and as a result, the first leg 33 connected to the ball housing 50 is rotated to fasten or release the screw coupling between the first leg 33 and the second leg 35 and thus change the length of the variable leg 30. Since a means for changing the length of the variable leg 30 does not exist in the variable leg 30 as described above, the variable leg 30 has a smaller volume and a smaller weight and is convenient to carry. Also, even though a variable leg not having metal material is applied or the variable leg has metal material partially, the area displayed on a radiographic image may be minimized, and thus a superior radiographic image may be obtained.

The fixing member 40 is a component for fixing a bone fragment of the fractured or deformed bone to the first frame 10 or the second frame 20. For fixing the bone fragment, the fixing member 40 may include a pin 43 stuck in the bone fragment and a fixture 45 for fixing the pin 43 onto the first frame 10 or the second frame 20. In the present disclosure, the fixing member 40 may be mounted on the first frame 10 serving as an upper frame and may fix the bone fragment with reference to the first frame 10.

The external fixator 80 according to an embodiment of the present disclosure has been described above. Hereinafter, an external fixing system according to an embodiment of the present disclosure will be described.

The external fixing system according to an embodiment of the present disclosure will be described with reference to FIGS. 7 to 11. FIG. 7 is a diagram showing an external fixing system according to an embodiment of the present disclosure. FIG. 8 is a diagram showing that a surgical actuator is coupled to an external fixator of the external fixing system according to an embodiment of the present disclosure. FIG. 9 is a diagram showing another example of the surgical actuator of the external fixing system according to an embodiment of the present disclosure. FIG. 10 is a perspective view showing a portable actuator of the external fixing system according to an embodiment of the present disclosure. FIG. 11 is a schematic view showing that a portable actuator and a ball housing of the external fixing system according to an embodiment of the present disclosure are coupled.

Referring to FIGS. 7 to 11, the external fixing system according to an embodiment of the present disclosure includes an external fixator 80, an actuator and a planning server 150.

The external fixator 80 may be the external fixator 80 according to an embodiment of the present disclosure, and the external fixator 80 may perform bone reduction by applying a force to a fractured or deformed bone.

The actuator is a driving device that changes the length of the variable leg 30 of the external fixator 80 and may include a surgical actuator 90 and a portable actuator 100. That is, the external fixing system of the present disclosure includes a detachable actuator, separate from the external fixator 80.

The surgical actuator 90 may be used in a surgical operation for the reduction of a fractured or deformed bone or may be used when the bond has a simple deformation to allow bone reduction by a one-step operation of a medical worker. The surgical actuator 90 may include a driving unit 97 having a motor 93 and a motor frame 91 to which the motor 93 is mounted.

Specifically, the driving unit 97 may include a motor 93 having an encoder attached thereto and a motor drive 95 connected to the motor 93 and serving as a power transmission member rotated by the power of the motor 93. Since the encoder is attached to the motor 93, it is possible to adjust the rotating direction and speed. Also, a protrusion is formed at an upper portion of the motor drive 95. The driving unit 97 rotates the ball housing 50 of the external fixator 80 to change the length of the variable leg 30. Seeing this mechanism, a lower space 65 is formed at a lower portion of the ball housing 50 and the protrusion of the motor drive 95 having a shape corresponding to the lower space 65 is fit into the lower space 65, so that the ball housing 50 and the motor drive 95 are moved integrally. In this configuration, the motor 93 provides a rotation force to the motor drive 95 to rotate the motor drive 95, and as a result, the ball housing 50 coupled to the motor drive 95 is also rotated.

In addition, as described above, the ball 55 connected to the first leg 33 is present in the ball housing 50 and united to the ball housing 50 by the pin member 63. Thus, if the ball housing 50 rotates by the driving unit 97, the first leg 33 connected to the ball 55 is rotated, and as a result, the first leg 33 moves into the second leg 35 along the rotation direction, thereby shortening the length of the variable leg 30, or the first leg 33 moves out of the second leg 35, thereby elongating the length of the variable leg 30.

Moreover, two driving unit 97, each including the motor 93 and the motor drive 95, may be bound by a mounting bracket to form one power group.

The motor frame 91 is a member at which the driving unit 97 having the motor 93 is installed. The shape of the motor frame 91 may be the same as the first frame 10 and the second frame 20. In the present disclosure, six variable legs 30 are provided, and accordingly six ball housings 50 are provided. Thus, six driving units 97 are installed at the motor frame 91. At this time, three power groups, each having two driving units 97, are installed at the motor frame 91, and on the motor frame 91, one power group is installed at a location corresponding to the ball housing 50 mounted to the second frame 20. Thus, when the surgical actuator 90 is mounted to the external fixator 80, the motor drive 95 of the surgical actuator 90 may be accurately fit into the lower space 65 of the ball housing 50.

Meanwhile, as seen from FIG. 9, similar to the first frame 10 and the second frame 20, the motor frame 120 may be composed of a plurality of sub frames 121, 123, 125, and the sub frames 121, 123, 125 may be connected using a coupling component such as a bolt and a nut. If the motor frame 120 is composed of a plurality of sub frames 121, 123, 125, after releasing the coupling between the sub frames 121, 125 and opening the released sub frames 121, 125, the motor frame 120, namely the actuator, may be easily located at the fractured or deformed part of the bond.

The portable actuator 100 may be used when progressive reduction is necessary in consideration of the recovery of nerves and blood vessels due to severe deformation of the bone, and is a driving member when a medical worker or a patient performs progressive bone reduction after surgical operation. The portable actuator 100 may be applied to patients with a large deformation angle or patients requiring bone lengthening (patients who take three to four months for curing and to whom a large strength should be stably maintained over a long period of time).

Meanwhile, after the surgical operation, the patient may carry the portable actuator 100 and perform the self bone reduction according to a progressive reduction plan. Thus, the patient may perform the bone reduction by himself/herself according to a predetermined plan stored in the planning server 150 without the help of a medical worker, which gives a lot of convenience.

As seen from FIG. 10, the portable actuator 100 may be composed of two driving units 110, each including a motor 105 and a motor drive 107. Two driving units 110 are bound together by a mounting bracket to form one power group, which serves as the portable actuator 100. Thus, as seen from FIG. 11, the portable actuator 100 may rotate two ball housings 50 at one bone reduction, thereby changing the length of two variable legs 30.

Meanwhile, in a conventional external fixator, in order to change the length of the variable leg, a direct drive mechanism and a motor are installed in a variable leg, but this increases the volume and weight of the variable leg and gives a limit to the maximum stroke of the variable leg. In addition, as the driving means is installed inside the variable leg, a metal component is present therein, which affects a radiographic image, thereby narrowing the field of the view image. As a result, the number of times of radiography increases, and the patient is more exposed to the radiation in order to observe the affected part.

Moreover, when performing progressive bone reduction after a surgical operation, the patient should carry an external fixator including a heavy and a large variable leg, which gives a great burden on the patient. Also, since the driving device is provided inside the variable leg, it is difficult to handle associated cables in the variable leg.

Meanwhile, in the present disclosure, a device for changing the length of the variable leg 30 is not present inside the variable leg 30, and the length of the variable leg 30 is changed using the actuator 90, 100, which is different from the external fixator 80. Thus, the variable leg 30 has a small volume and weight, and thus it is easy to carry and manage the external fixator 80. Also, even though the variable leg 30 contains no metal material or some metal material, the area displayed on the radiographic image may be minimized, thereby ensuring a superior radiographic image. Also, as the number of times of radiography is reduced, the patient is less exposed to the radiation. In addition, for the progressive bone reduction, the external fixator 80 mounted on the patient has a small weight and thus it is easy to carry, and thereby no difficulty in arranging cables.

The planning server 150 is a server for controlling operation of the actuators 90, 100 and for controlling a rotation force provided by the actuators 90, 100. In the present disclosure, the planning server 150 may determine which driving unit among the six driving units 97 of the surgical actuator 90 should be operated and determine which driving unit of the two driving units 110 of the portable actuator 100 should be operated. Also, if any driving unit is operated, the planning server 150 may determine when the driving unit should be operated and determine the rotation force and the rotation direction of the driving units 97, 110.

Since the operating plan for the actuators 90, 100 are set in the planning server 150 in advance, the external fixation surgery is performed according to the operation plan or the progressive bone reduction is performed after the surgical operation. Thus, the length of the variable leg 30 may be changed by an accurate amount, and as a result, it is possible to ensure a successful surgical operation by applying a desired amount of force to the affected part. Also, during the progressive bone reduction process, a proper reduction process may be performed even though the patient does not care much.

Additionally, the external fixing system according to the present disclosure may include a workstation, which may include an indicator that displays information relating to the progress of a surgical operation. Thus, a medical worker may check a state of the fractured or deformed bone, the progress of the external fixation surgery, and the operation plan of the actuators 90, 100, or the like through the workstation, thereby ensuring the medical worker to easily perform the surgical operation.

The embodiments of the present disclosure have been described with reference to the accompanying drawings, but it will be understood by those skilled in the art that the present disclosure can be implemented in other specific forms without departing from the scope or essential characteristics thereof. Therefore, it should be understood that the embodiments described above are not restrictive but illustrative in all aspects.

The invention claimed is:

1. An external fixator for reduction of a fractured or deformed bone, comprising:
   a first frame having a configuration through which a bone passes;
   a second frame having a configuration through which the bone passes, the second frame being spaced apart from the first frame; and
   a variable leg connected to the second frame by a ball joint, the variable leg having a first leg and a second leg, each of the first leg and the second leg having a thread thereon,
   wherein the ball joint includes a ball connected to the first leg through a ball axle, the ball having a perforation hole passing through a center thereof, a ball housing located at the second frame, the ball housing having a fitting groove into which the ball is accommodated and a pair of insert holes defined at an outer surface of the ball housing along a direction traversing the fitting groove to face each other, and a pin provided to extend over the pair of the insert holes to pass through the perforation hole,
   wherein the second frame has a top surface, which faces a bottom surface of the first frame, and the ball housing is positioned on the top surface of the second frame, and wherein as the ball housing rotates, the first leg rotates to fasten or release screw coupling between the first leg and the second leg and to change a length of the variable leg.

2. The external fixator according to claim 1, wherein a male thread is defined at the first leg, and a female thread is defined at the second leg.

3. The external fixator according to claim 1, wherein the perforation hole has the same diameter as the pin at the center, and a portion of the perforation hole on a spherical surface of the ball has a greater area than a sectional area of the pin.

4. The external fixator according to claim 3, wherein the perforation hole has a symmetrical shape with respect to the center, and a vertical section of the symmetrical shape gradually decreases from the spherical surface toward the center.

5. The external fixator according to claim 1, wherein a shaft fixing device is located on the first leg to be configured to have a screw coupling with the first leg, and the shaft fixing device prevents the first leg from moving with respect to the second leg.

6. The external fixator according to claim 1, further comprising:
a fixing structure configured to fix a bone fragment of the bone to the first frame or the second frame,
wherein the fixing structure includes a fixing pin stuck in the bone fragment and a fixture to attach the fixing pin to the first frame or the second frame.

7. An external fixing system comprising:
an external fixator having:
a first frame having a configuration through which a bone passes,
a second frame having a configuration through which the bone passes, the second frame being spaced apart from the first frame, and
a variable leg connected to the second frame by a ball joint, the variable leg having a first leg and a second leg, each of the first leg and the second leg having a thread thereon,
wherein the ball joint includes a ball connected to the first leg through a ball axle, the ball having a perforation hole passing through a center thereof, a ball housing located at the second frame, the ball housing having a fitting groove into which the ball is accommodated and a pair of insert holes defined at an outer surface of the ball housing along a direction traversing the fitting groove to face each other, and a pin provided to extend over the pair of the insert holes to pass through the perforation hole,
wherein the second frame has a top surface, which faces a bottom surface of the first frame, and the ball housing is positioned on the top surface of the second frame, and
wherein as the ball housing rotates, the first leg rotates to fasten or release screw coupling between the first leg and the second leg and to change a length of the variable leg; and
a detachable actuator configured to give a power to rotate the ball housing,
wherein the actuator includes a motor and a power transmission rotated by the motor, and a protrusion of the power transmission is inserted into a lower space of the ball housing and the ball housing rotates by a rotation force of the actuator.

8. The external fixing system according to claim 7, wherein the actuator is a surgical actuator and includes a driving assembly having the motor and the power transmission, a number of each of the motor and the power transmission is the same with that of the ball housing, and the driving assembly rotates the ball housing corresponding thereto.

9. The external fixing system according to claim 7, wherein the actuator is a portable actuator used for progressive revision.

10. The external fixing system according to claim 9, wherein the portable actuator includes two driving assemblies, each of the two driving assemblies having the motor and the power transmission member.

11. An external fixing system comprising:
an external fixator having:
a first frame having a configuration through which a bone passes,
a second frame having a configuration through which the bone passes, the second frame being spaced apart from the first frame, and
a variable leg connected to the second frame by a ball joint, the variable leg having a first leg and a second leg, each of the first leg and the second leg having a thread thereon,
wherein the ball joint includes a ball connected to the first leg through a ball axle, the ball having a perforation hole passing through a center thereof, a ball housing located at the second frame, the ball housing having a fitting groove into which the ball is accommodated and a pair of insert holes defined at an outer surface of the ball housing along a direction traversing the fitting groove to face each other, and a pin provided to extend over the pair of the insert holes to pass through the perforation hole,
wherein the second frame has a top surface, which faces a bottom surface of the first frame, and the ball housing is positioned on the top surface of the second frame, and
wherein as the ball housing rotates, the first leg rotates to fasten or release screw coupling between the first leg and the second leg and to change a length of the variable leg;
a detachable actuator configured to give a power to rotate the ball housing and having a motor and a power transmission rotated by the motor; and
a planning server configured to select the motor to be operated and control a rotation force and a rotation direction of the motor,
wherein a protrusion of the power transmission is inserted into a lower space of the ball housing and the ball housing rotates by a rotation force of the actuator.

12. The external fixing system according to claim 11, wherein the actuator is a surgical actuator and includes a driving assembly having the motor and the power transmission, a number of each of the motor and the power transmission is the same with that of the ball housing, and each of the driving assemblies rotates a ball housing corresponding thereto.

13. The external fixing system according to claim 12, wherein the surgical actuator further includes a motor frame at which the driving assembly is installed, and the motor frame has the same shape as the second frame and is composed of a plurality of sub frames.

14. The external fixing system according to claim 11, wherein the actuator is a portable actuator used for progressive revision.

15. The external fixing system according to claim 14, wherein the portable actuator includes two driving assemblies, each of the two driving assemblies having the motor and the power transmission member.

16. The external fixing system according to claim 14, wherein an operating plan of the portable actuator is set in the planning server, and the planning server controls the portable actuator according to the operating plan.

* * * * *